United States Patent [19]

Schutz et al.

[11] 3,989,844
[45] Nov. 2, 1976

[54] BASIC OXIMES AND THEIR PREPARATION

[75] Inventors: Siegismund Schutz; Otto Behner; Friedrich Hoffmeister, all of Wuppertal-Elberfeld, Germany

[73] Assignee: Bayer Aktiengesellschaft, Germany

[22] Filed: June 11, 1971

[21] Appl. No.: 152,449

Related U.S. Application Data

[60] Division of Ser. No. 849,539, July 14, 1969, which is a continuation of Ser. No. 587,696, Oct. 19, 1966, abandoned.

[30] Foreign Application Priority Data

Nov. 10, 1965 Germany.............................. 47635

[52] U.S. Cl. .............................................. 424/327
[51] Int. Cl.² ......................................... A61K 31/15
[58] Field of Search ........................... 424/326, 327; 260/566 AE, 501.4

[56] References Cited
UNITED STATES PATENTS

| | | | |
|---|---|---|---|
| 3,270,055 | 8/1966 | Engelhard et al. ........... | 260/566 AE |
| 3,349,128 | 10/1967 | Judd .............................. | 260/566 AE |
| 3,441,608 | 4/1969 | Shutz et al. ................... | 260/566 AE |
| 3,526,631 | 9/1970 | Judd .............................. | 260/566 AE |
| 3,526,671 | 9/1970 | Judd .............................. | 260/566 AE |

*Primary Examiner*—Stanley J. Friedman

[57] ABSTRACT

Oximes of the formula:

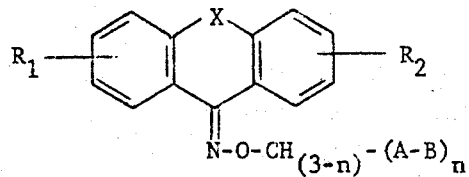

and their acid salts, wherein A is a branched or unbranched, saturated or unsaturated alkylene chain of 0–6 carbon atoms, B is a basic nitrogen-containing group such as an amino, alkylamino, dialkylamino, cycloalkylamino, dicycloalkylamino, cycloalkylalkylamino, dicycloalkylalkylamino, alkylarylamino, alkylaralkylamino, a piperidino, pyrrolidino, hexamethyleneimino, morpholino, thiomorpholino, N-alkylpiperazino or N-(2-hydroxyalkyl)-piperazino group, $n$ is 1 or 2 and X is $-CH_2-$, $-(CH_2)_3-$ or $-CH=CH-$, and $R_1$ and $R_2$ are each hydrogen, halogen, alkyl of 1–4 carbon atoms, alkoxy, alkylmercapto groups of 1–4 carbon atoms, hydroxyl, nitro, amino or trifluoromethyl, are useful for their anti-depressant activity. Pharmaceutical compositions may be prepared which comprise an anti-depressant amount of at least one such compound in combination with a pharmaceutically acceptable inert diluent or carrier. Depression in humans and animals may be treated by administering an anti-depressant amount of such an oxime to such human or animal.

6 Claims, No Drawings

BASIC OXIMES AND THEIR PREPARATION

This is a divisional of our copending application Ser. No. 849,539 filed July 14, 1969 which is a continuation of our application Ser. No. 587,696 filed Oct. 19, 1966, now abandoned.

The present invention relates to novel basic oximes and their acid salts having anti-depressive activity and to procedure for preparing the same.

It is known that basic-substituted oximes of 10,11-dihydro-5H-dibenzo[a,d]-cycloheptene-5-one possess a thymoleptic action (DAS No. 1,198,353). S. Rossi and co-workers (Farmaco Ed. Sc. XIX 688–702 and ibid. XX 25–35) have also shown that a number of further basic oximes have a parasympatholytic and spasmolytic action.

We have now discovered novel, pharmacologically useful basic oximes of the formula:

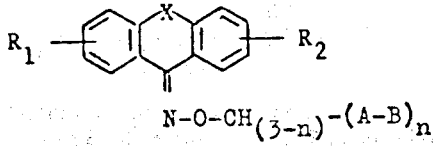

wherein A is a branched or unbranched, saturated or unsaturated alkylene chain of 0–6 carbon atoms, B is a basic nitrogen-containing group such as an amino, alkylamino, dialkylamino, cycloalkylamino, dicycloalkylamino, cycloalkylalkylamino, dicycloalkylalkylamino, alkylarylamino, alkylaralkylamino, a piperidino, pyrrolidino, hexamethyleneimino, morpholino, thiomorpholino, N-alkylpiperazino or N-(2-hydroxyalkyl)-pipera piperazino group, $n$ is 1 or 2 and X is $-CH_2-$, $-(CH_2)_3-$ or $-CH=CH-$, and $R_1$ and $R_2$ are each hydrogen, halogen, alkyl of 1–4 carbon atoms, alkoxy, alkylmercapto groups of 1–4 carbon atoms, hydroxyl, nitro, amino or trifluoromethyl.

These compounds have remarkable pharmacological properties and, also in animal experiments, reveal activity qualities from which there can be deduced, inter alia, a considerable antidepressive action in humans. The compounds are administered in a therapeutically effective amount in the same general manner as known antidepressants.

The compounds can be used as such or in the form of their salts with non-toxic pharmaceutically acceptable inorganic or organic acids.

Acids suitable for the salt formation are e.g. acetic acid, propionic acid, lactic acid, maleic acid, fumaric acid, succinic acid, tartaric acid, citric acid, salicylic acid, naphthalene-1,5-disulphonic acid, phosphoric acid, hydrochloric acid, etc.

The new compounds are prepared by reacting in known manner a ketone of the formula:

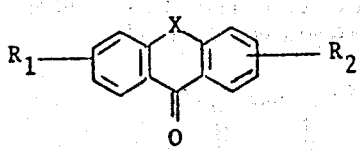

or a reactive derivative thereof such as a ketal, chloride or corresponding thio compound 1. with a hydroxyamine of the formula:

$$H_2N-O-CH_{(3+n)}-(A-B)_n$$ or 2. first converting the ketone or reactive derivative with hydroxylamine into an oxime of the formula:

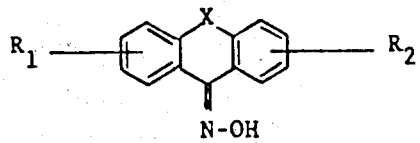

and reacting such in the form of a suitable metal salt with a halide of the formula:

$$halogen-CH_{(3+n)}-(A-B)_n$$ or 3. partially reacting an oxime of the formula:

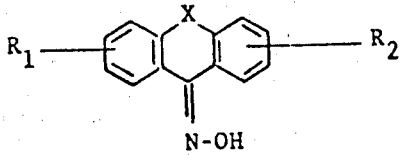

with a dihalide of the formula:

$$halogen-CH_2-A-halogen$$

and then reacting the resulting compound of the formula:

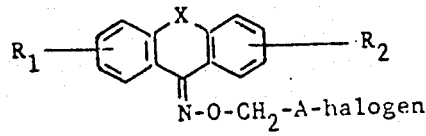

with an amine of the formula:

$$H-B$$

wherein, in the above formulas, A, B, $n$, X, $R_1$ and $R_2$ have the previously designated meanings.

The invention is illustrated by the following non-limitative examples.

EXAMPLE 1

1.15 g of sodium are dissolved in 100 ml of absolute ethanol; 10 g of 5-oximino-5H-dibenzo[a,d]cycloheptene are introduced and boiling under reflux is effected for 1 hour. 6.4 g of β-dimethylaminoethyl chloride are then added dropwise at room temperature. This is followed by heating to the boil and boiling under reflux for 1½ hours. Finally, the mixture is evaporated to dryness, the residue dissolved in ether/water and the ethereal phase washed with water. After drying of the ethereal phase with potassium carbonate, the hydrochloride of 5-β-dimethylamino-ethoxyimino-5H-dibenzo[a,d]cycloheptene (melting point 230° C) can be obtained from the solution with HCl.

EXAMPLE 2

1.15 g of Na are dissolved in 100 ml of absolute ethanol; 10 g of 5-oximino-5H-dibenzo[a,d]cycloheptene are introduced, followed by boiling under reflux for 1 hour and evaporation to dryness. The residue is dissolved in dimethylformamide and part of the solvent is distilled off. The solution is now cooled to about 20° C and there are added 5.3 g of methylaminoethyl chloride which is prepared below 10° C from the corresponding hydrochloride by supersaturation with potassium carbonate. The mixture is then heated to 100° C for 1½ hours. Upon further working up analogous to Example 1 being effected, 8.5 g of the hydrochloride of 5-β-methylaminoethoxyimino-5H-dibenzo[a,d]cycloheptene (melting point 232°–233° C) are obtained.

EXAMPLE 3

1.15 g of sodium are dissolved in 100 ml of absolute ethanol; 11.9 g of 12-oximino-5,6,7-12-tetrahydrodibenzo-[a,d]cyclooctene are introduced and boiling under reflux is effected for 1 hour. 8.1 g of β-piperidino-ethylchloride are then added dropwise at room temperature. The mixture is slowly heated to the boil and boiling is continued under reflux for 2 hours. Finally, the mixture is evaporated to dryness, the residue taken up in acetic acid (10%), separated from insoluble constituents by filtering, the base precipitated by addition of concentrated sodium hydroxide solution and taken up in ether. Drying with potassium carbonate is followed by evaporation to dryness, the residue is dissolved in acetone, a solution of naphthalene-1,5-disulfonic acid in acetone is added whereupon the salt of 12-β-piperidinoethoxy-imino-5,6,7-12-tetrahydrodibenzo[a,d]cyclooctene with ½ naphthalene-1,5-disulfonic acid precipitates in crystalline form. Melting point 189°–194° C; yield 10.4 g.

In analogous manner there are obtained with 6.7 g of β-dimethylaminopropylchloride, 3.5 g of the salt of 12-β-dimethylaminoethoxyimino-5,6,7-12-tetrahydrodibenzo-[a,d]cyclooctene with ½ naphthalene-disulfonic acid of the melting point 190°–193° C.

EXAMPLE 4

10.3 g of 5H-dibenzo[a,d]cycloheptenone-(5) and 35.4 g of β-dimethylaminoethoxyamine-dihydrochloride are dissolved in 200 ml of absolute pyridine and the solution is boiled under reflux for 24 hours. The mixture is then evaporated to dryness, the residue taken up in acetic acid (about 10%) and the turbid solution filtered. By addition of concentrated sodium hydroxide solution the base is precipitated from the filtrate and taken up in ether. Drying the solution with sodium carbonate is followed by evaporation to dryness, the residue is dissolved in ether and the hydrochloride of 5-β-dimethylaminoethoxy-imino-5H-dibenzo[a,d]cycloheptene of the melting point 230° C is precipitated by introducing HCl gas. Yield 11.7 g.

EXAMPLE 5

1.15 g of sodium are dissolved in 100 ml of absolute ethanol and 10 g of 5-oximino-5H-dibenzo[a,d]cycloheptene are added to the solution. The solution is introduced into a boiling solution of 90 g of 1,2-dibromoethane in 200 ml of absolute ethanol within 3 hours. The solution is refluxed with stirring for 3 hours, evaporated to dryness in vacuum, the residue added to a solution of 3 g of methylamine in 150 ml of absolute ethanol and heated in an autoclave to 120° C for 9 hours. Finally, the mixture is evaporated to dryness and worked up analogously to Example 4. 9.6 g of the hydrochloride of 5-β-methylamino-ethoxyimino-5H-dibenzo[a,d]cycloheptene of the melting point 232° C are obtained.

What is claimed is:

1. An antidepressant composition which comprises an antidepressant amount of a compound of the formula:

or a pharmaceutically acceptable non-toxic acid salt thereof in combination with a pharmaceutically acceptable inert diluent or carrier.

2. An antidepressant composition according to claim 1 wherein the compound is

3. An antidepressant composition according to claim 1 wherein the compound is the hydrochloride salt of 4. A method of treating depression in humans and animals which comprises administering to a human or animal in need thereof an antidepressant amount of a compound of the formula:

or a pharmaceutically acceptable non-toxic acid salt thereof.

5. A method according to claim 4 wherein the compound is

6. A method according to claim 4 wherein the compound is the hydrochloride salt of

* * * * *